US00PP12490P2

(12) United States Plant Patent

Olesen et al.

(10) Patent No.: US PP12,490 P2
(45) Date of Patent: Mar. 26, 2002

(54) MINIATURE ROSE PLANT NAMED 'POULMO'

(76) Inventors: L. Pernille Olesen; Mogens N. Olesen, both of Hillerødvejen 49, Fredensborg (DK), DK-3480

( * ) Notice: Subject to any disclaimer, the term of this patent is extended or adjusted under 35 U.S.C. 154(b) by 0 days.

(21) Appl. No.: 09/282,072

(22) Filed: Mar. 29, 1999

(51) Int. Cl.[7] ..... A01H 5/00
(52) U.S. Cl. ..... Plt./122
(58) Field of Search ..... Plt./122, 116

(56) References Cited

PUBLICATIONS

Plant Variety Office "Application For Plant Variety Rights" Jul. 23, 1992 Denmark.
Plant Variety Rights Office "Grant of Plant Variety Rights" Jan. 28, 1994 Denmark.
Community Plant Variety Office "Notice on the Grant Of Plant Variety Rights" Aug. 8, 1996 EU.
Community Plant Variety Office "Chapter 2: Variety Denominations" Feb. 26, 1996 EU.
Community Plant Variety Office "Table IV.I.2: Grants . . . " Oct. 15, 1996 EU.
Community Plant Variety Office "Receipt" Jul. 25, 1995 EU.
Research Center for Cultivar Testing "Decision" Feb. 24, 2000 Poland.
UPOV–ROM GTITM Computer Database 2000/06, Dec. 8, 2000, GTI Jouve Retrieval Software, citation for 'Poulmo'.*

* cited by examiner

*Primary Examiner*—Bruce R. Campell
*Assistant Examiner*—June Hwu

(57) ABSTRACT

A new garden rose plant which has abundant, dark-red flowers and attractive, disease resistant foliage. This new and distinct variety has shown to be uniform and stable in the resulting generations from asexual propagation.

1 Drawing Sheet

SUMMARY OF THE INVENTION

The present invention constitutes a new and distinct variety of garden rose plant which originated from a controlled crossing between an 'POULander' (U.S. Plant Pat. No. 6,265) and 'Red Minimo' (U.S. Plant Pat. No. 5,770). The two parents were crossed and the resulting seeds were planted in a controlled environment. The new variety is named 'POULmo'.

The new rose may be distinguished from its seed parent, 'POULander', by the following combination of characteristics:

1. The seed parent is a floribunda and the habit and size of the seed parent is much larger when compared to 'POULmo';

2. The seed parent has semi-double flowers; whereas, 'POULmo' has double flowers;

3. The seed patent carries its bloom in trusses along the stem; whereas 'POULmo' carries its flowers on the top of the plant in sprays.

The new variety may be distinguished from its pollen parent, 'Red Minimo' by the following combination of characteristics:

1. The blooms of the pollen parent have 15 to 20 petals; where as, 'POULmo's' petalage is double is 18–25 petals;

2. The color of the blooms of the pollen parent are orange-red, while the blooms of 'POULmo' are dark red.

The objective of the hybridization of this rose variety for garden use was to create a new and distinct variety with unique qualities, such as:

1. Uniform and abundant flowers;

2. Vigorous, compact growth;

3. Disease resistance;

4. Continuous blooming.

This combination of qualities is not present in previously available commercial cultivars of this type and distinguishes 'POULmo' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULmo' was selected in the spring of 1988 by the inventors as a single plant from the progeny of the aforementioned hybridization. Asexual reproduction of 'POULmo' by cuttings and traditional budding was first done by L. Pernille and Mogens N. Olesen in August 1988. This initial and other subsequent propagations conducted in controlled environments have demonstrated that the characteristics of 'POULmo' are true to type and are transmitted from one generation to the next.

BRIEF DESCRIPTION OF THE DRAWING

The accompanying color illustration shows, as true as is reasonably possible to obtain in color photographs of this type, the typical characteristics of the buds, flowers, leaves, and stems, of 'POULmo'. Specifically illustrated in SHEET 1:

1. Stem of plant showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULmo', as observed in its outdoor growth in a field nursery in Jackson County, Oreg., on plants aged eighteen months. Observations were conducted during October, 1998. Color references are made using The Royal Horticultural Society (London, England) Colour Chart, 1995, except where common terms of color are used.

For a comparison, several physical characteristics of the rose variety 'POULchris', a miniature floribunda rose variety from the same inventors described and illustrated U.S. Plant Pat. No. 11,151 dated Aug. 29, 1997 are compared to 'POULmo' in Chart 1.

CHART 1

| | 'POULmo' | 'POULchris' |
|---|---|---|
| Color of upper surface of open flower. | Red Group 45A. | Red Group 53A. |
| Petalage. | Double, 18–25 petals. | Very double, 55–65 petals. |
| Size (diameter) of open flower. | 35–40 mm. | 60 mm. |

Parents:
*Seed parent.*—'POULander'.
*Pollen parent.*—'Red Minimo'.
Classification:
*Botanical.*—*Rosa hybrida.*
*Commercial.*—Miniature.

FLOWER AND FLOWER BUD

Blooming habit: Continuous.
Flower bud:
*Size.*—Upon opening, 22 mm–24 mm in length from base of receptacle to end of bud.
*Bud form.*—Pointed ovoid to globular.
*Bud color.*—As sepals unfold, Red Group 46A. Red Group 46A at ¼ opening.
*Sepals.*—Upper side: Green Group 144A to 146B. Lower side: Green Group 144A to 146B. Many sepals have intonations of Greyed-Red Group 181A, on upper and lower surfaces. Moderate to strong foliaceous appendages. Surfaces of sepals moderately pubescent. Stipitate glands are abundant on margins and exterior of sepals. Sepals are 10 to 13 mm long and 10 mm wide. Sepals are cirrose at apex, with a flat base where they join with the receptacle.
*Receptacle.*—Surface: Smooth to lightly pubescent. Many with stipitate glands. Shape: Funnel shaped. Size: Small to medium, 5 mm (l)×5–6 mm (w). Color: Yellow-Green Group 146B.
*Peduncle.*—Surface: Generally smooth, with stipitate glands. Length: 30–35 mm average length. Color: Yellow-Green Group 146B, many with intonations of Greyed-Red Group 181A. Strength: Strong.
*Borne.*—Multiple buds per stem, with strong sprays of 8 to 10 buds per flowering stem.

Flower bloom:
*Fragrance.*—Little or no fragrance.
*Duration.*—As a cut flower 3 to 5 days. The blooms have a duration on the plant of approximately 4 to 7 days. Petals fall cleanly away from plant.
*Size.*—Average flower diameter is 35–40 mm when open.
*Form.*—Shape of flower when viewed from the side: Upon opening, upper part: Flat to flattened convex. Upon opening, lower part: Convex. Open flower, upper part: Flattened convex. Open flower, lower part: Flattened Convex.
*Petalage.*—Double, with 18–22 petals under normal conditions and 3–4 petaloids.
Color:
*Upon opening, petals.*—Upper Surface: Red Group 46A. Reverse Side: Red Group 53A–53B.
*Upon opening, basal petal spots.*—Outer Side: Yellow Group 1D. Inner Side: Orange-White Group 159D to White 155C.
*After opening, petals.*—Upper Surface: Red Group 45A. Reverse Side: Outermost petals Red Group 44A; innermost petals Red Group 53C.
*After opening, basal petal spots.*—Outer Side: White Group 155C. Inner Side: White Group 155C.
General tonality: On open flower Red Group 45A. No change in the general tonality at the end of the 2nd to 3rd day. Afterwards, general tonality is Red Group 46B.
Petals:
*Petal reflex.*—Petals often cupped in center but do not reflex.
*Petal edge.*—Entire, often with indentation in center of the margin.
*Shape.*—Outermost petals obovate, innermost petals are oblanceolate.
*Petaloids.*—Quantity: 3–4. Color: Red Group 53C. Texture: Smooth. Size: 5 to 8 mm and 5 to 7 mm wide.
*Texture.*—Thick.
*Arrangement.*—Imbricated.
Reproductive organs:
*Pistils.*—Quantity: 30 to 35. Size: 5 to 7 mm long.
*Pollen.*—Color: Yellow-Orange Group 15C–15D. Quantity: Average.
*Anthers.*—Size: 2 to 4 mm long. Color: Mature: Yellow Group 12C. Immature: Greyed-Orange Group 164C and Brown Group 200D. Quantity: 30 to 40.
*Filaments.*—Color: Yellow Group 1B–1C. Length: 3 to 5 mm long.
*Stigmas.*—Slightly superior in location to anthers. Color: Yellow-Green Group 145D.
*Styles.*—Color: Green-White Group 157B.
*Hips.*—None observed.

PLANT

Plant growth: Vigorous, compact, upright to bushy. When grown as a budded field grown plant on *Rosa multiflora* understock, the average height of the plant itself is 50 cm and the average width is 60 cm.
Stems:
*Color.*—Young wood: Yellow-Green Group 144B. Older wood: Yellow-Green Group 146B.
*Thorns.*—Incidence: 15 to 20 thorns per 10 cm of stem. Size: Variable, finer and smaller thorns of 1–2 mm in length on the upper stems and longer 4 mm thorns on more mature stems. Color: Yellow-Green Group 145D. Shape: Linear with slight downward curve.

*Surface.*—Young wood: Smooth. Older wood: Smooth.

Plant foliage: Normal number of leaflets on leaves in middle of the stem: 5 leaflets.

*Leaf size.*—Medium. 75–85 mm (l)×50–60 mm (w).

*Quantity.*—Average.

*Color.*—Upper Leaf Surface: Green Group 137A. Lower Leaf Surface: Yellow-Green Group 146C and Yellow-Green Group 147C. Juvenile foliage: Upper surface is Yellow-Green Group 146A and Yellow-Green Group 147A. Lower surface is Green Group 138C. Anthocyanin: Location: Immature foliage and stems. Color: Greyed-Purple Group 183B.

Plant leaves and leaflets:

*Stipules.*—Size: 14 mm–16 mm. Color: Green Group 137C. Stipitate glands: Present on margins.

*Petiole.*—Length: 20 mm–25 mm. Color: Green Group 137C. Underneath: Smooth. Margins: With stipitate glands.

*Rachis.*—Color: Green Group 137B. Underneath: Smooth with 1–2 small prickles. Margins: With stipitate glands.

*Leaflet.*—Leaflet: Edge: Serrated. Shape: Ovate. The leaflet's apex is acuminate. The leaflet's base is rounded. Arrangement: The leaflets are arranged in an odd-pinnate formation. Venation: The leaflets are veined in a reticulate pattern. Texture: Upper side of leaflet is slightly glossy, leathery. Margins of basal area have stipitate glands.

Disease resistance: Average resistance to mildew, black spot, and under normal growing conditions in Jackson County, Oreg.

Cold hardiness: 'POULmo' has been found to be resistant to damage from cold in USDA Zone 8 and USDA Zone 7.

We claim:

1. A new and distinct variety of rose plant of the miniature class, substantially as herein illustrated and described as a distinct and novel rose variety due to its abundant, dark-red flowers, vigorous growth, disease resistance, and extended period of bloom.

* * * * *

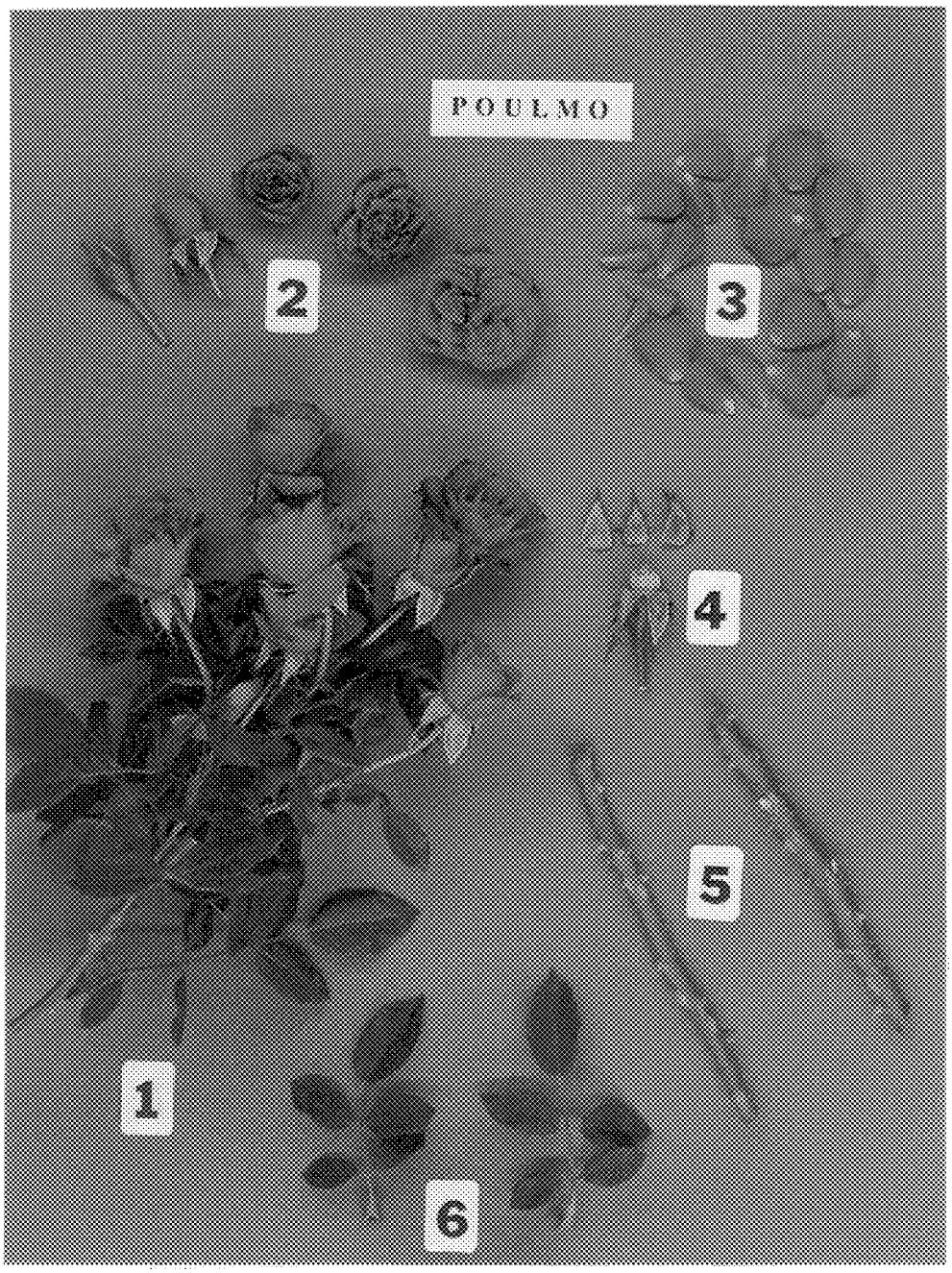
POULMO
2
3
4
5
1
6